United States Patent
Zhong

(10) Patent No.: US 7,913,838 B2
(45) Date of Patent: Mar. 29, 2011

(54) PACKAGING CONTAINER FOR TEST SENSORS

(75) Inventor: Weiping Zhong, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 311 days.

(21) Appl. No.: 11/885,952

(22) PCT Filed: Mar. 21, 2006

(86) PCT No.: PCT/US2006/010282
§ 371 (c)(1),
(2), (4) Date: Sep. 7, 2007

(87) PCT Pub. No.: WO2006/102348
PCT Pub. Date: Sep. 28, 2006

(65) Prior Publication Data
US 2008/0164164 A1    Jul. 10, 2008

Related U.S. Application Data

(60) Provisional application No. 60/664,304, filed on Mar. 22, 2005.

(51) Int. Cl.
*A61B 17/32* (2006.01)
(52) U.S. Cl. .................. 206/305; 206/569; 600/583
(58) Field of Classification Search .................. 206/305, 206/569, 363, 365, 366, 367; 600/583, 584
See application file for complete search history.

(56) References Cited

U.S. PATENT DOCUMENTS

| | | | |
|---|---|---|---|
| 5,510,266 A | 4/1996 | Bonner et al. ................. | 436/43 |
| 5,575,403 A | 11/1996 | Charlton et al. ............... | 221/31 |
| 5,632,410 A | 5/1997 | Moulton et al. ................ | 221/79 |
| 5,645,798 A | 7/1997 | Schreiber et al. .............. | 422/58 |
| 5,660,791 A | 8/1997 | Brenneman et al. ........... | 422/58 |

(Continued)

FOREIGN PATENT DOCUMENTS

EP    1285695 A    2/2003

(Continued)

OTHER PUBLICATIONS

Written Opinion of the International Searching Authority corresponding to co-pending International Patent Application No. PCT/US2006/010282, European Patent Office, dated Jul. 31, 2006, 6 pages.

(Continued)

*Primary Examiner* — Jacob K Ackun, Jr.
(74) *Attorney, Agent, or Firm* — Nixon Peabody LLP

(57) ABSTRACT

A test sensor packaging container for use in sensor instrument. The test sensor packaging container comprises a housing, a first foil cover, and a second foil cover. The housing has a plurality of test sensor containing regions. Each of the test sensor containing regions has a proximal end and a distal end and is adapted to contain a test sensor. The test sensor containing regions protrude radially outward from the center of the housing. The housing has a top portion and a bottom portion that are generally parallel. Each of the test sensors has a width direction and a thickness direction. The first foil cover is adapted to cover the top portion of the housing. The second foil cover is adapted to cover the distal end of the plurality of test sensor containing regions. A plane generally parallel to the width direction of each of the plurality of test sensors is generally perpendicular to the top and bottom portion of the housing.

22 Claims, 6 Drawing Sheets

U.S. PATENT DOCUMENTS

| | | | |
|---|---|---|---|
| 5,720,924 A | 2/1998 | Eikmeier et al. | 422/102 |
| 5,863,800 A | 1/1999 | Eikmeier et al. | 436/48 |
| 6,497,845 B1 | 12/2002 | Sacherer | 422/104 |
| 2003/0059350 A1 | 3/2003 | Sacherer | 422/104 |
| 2004/0047764 A1 | 3/2004 | Purcell | 422/58 |
| 2004/0092995 A1 | 5/2004 | Boecker et al. | 606/181 |
| 2004/0094564 A1* | 5/2004 | Papp | 221/25 |
| 2004/0230216 A1* | 11/2004 | Levaughn et al. | 606/181 |
| 2005/0027211 A1 | 2/2005 | Kuhr et al. | 600/583 |
| 2006/0184065 A1* | 8/2006 | Deshmukh et al. | 600/583 |
| 2006/0241666 A1* | 10/2006 | Briggs et al. | 606/181 |
| 2006/0276724 A1* | 12/2006 | Freeman et al. | 600/583 |

FOREIGN PATENT DOCUMENTS

| | | |
|---|---|---|
| EP | 1 475 630 A1 | 11/2004 |
| WO | WO 2006/035322 A2 | 4/2006 |

OTHER PUBLICATIONS

International Search Report corresponding to co-pending International Patent Application No. PCT/US2006/010282, European Patent Office, dated Jul. 31, 2006, 4 pages.

* cited by examiner

PACKAGING CONTAINER FOR TEST SENSORS

CROSS-REFERENCE TO RELATED APPLICATIONS

This application claims priority to Application No. 60/664,304 filed on Mar. 22, 2005, which is incorporated by reference in its entirety.

FIELD OF THE INVENTION

The present invention relates generally to a packaging container for test sensors and, more particularly, to a circular packaging container for test sensors to be used in conjunction with a liquid sample monitoring device to provide an analyte concentration in a liquid sample.

BACKGROUND OF THE INVENTION

Individuals who have irregular blood glucose concentration levels are often medically required to self-monitor their blood glucose concentration level. An irregular blood glucose level can be brought on by a variety of reasons, including illness, such as diabetes. The purpose of monitoring the blood glucose level is to determine the concentration level and then to take corrective action, based on whether the level is too high or too low, to bring the level back within a normal range. The failure to take corrective action may have serious adverse effects on the individual.

Beyond the above-described blood glucose concentration level monitoring, self-testing systems are used for determining the presence or concentration of other analytes in body fluids, such as, for example, cholesterol, alcohol, and hemoglobin in blood, interstitial fluid, or chemical substances in saliva.

One method of monitoring a person's blood glucose level is with a portable, hand-held, blood glucose testing device. The portable nature of these devices enables users to conveniently test their blood glucose levels wherever the users may be. The test device receives a test sensor for harvesting the blood for analysis. The test sensor, one of which is required for each test, contains a reaction area including a reagent for producing a measurable reaction with the glucose indicative of the blood glucose concentration level. The test sensor harvests the blood for reaction with the reagent stored within.

Prior art test devices exist that contain a plurality of test sensors or test strips in either a circular sensor packaging container or a cartridge sensor packaging container. An exemplary prior art circular sensor packaging container is disclosed in U.S. Pat. No. 5,575,403. In the prior art devices, a plane parallel to the width of the test sensor is parallel to a plane running through the top portion of the housing of the sensor packaging container One drawback with prior art circular sensor packaging container is the limited number of test sensors contained in the container. The number of test sensors contained in the sensor packaging container is limited by the physical space available for the sensor packaging container within the handheld test device. Therefore, a need exists for a circular sensor packaging container that contains a greater number of test sensors without needing to dramatically increase the physical space taken up within the handheld test device by the circular sensor packaging container.

SUMMARY OF THE INVENTION

According to one embodiment of the present invention, a test sensor packaging container for use in sensor instrument is provided. The test sensor packaging container comprises a housing, a first foil cover, and a second foil cover. The housing has a plurality of test sensor containing regions. Each of the test sensor containing regions has a proximal end and a distal end and is adapted to contain a test sensor. The test sensor containing regions protrude radially outward from the center of the housing. The housing has a top portion and a bottom portion that are generally parallel. Each of the test sensors has a width direction and a thickness direction. The first foil cover is adapted to cover the top portion of the housing. The second foil cover is adapted to cover the distal end of the plurality of test sensor containing regions. A plane generally parallel to the width direction of each of the plurality of test sensors is generally perpendicular to the top and bottom portion of the housing.

According to another embodiment of the present invention, a test sensor packaging container for use in sensor instrument is provided. The test sensor packaging container comprises a housing, a first foil cover, and a second foil cover. The housing has a plurality of test sensor containing regions and a plurality of desiccant cavities in fluid communication with each of the test sensor containing regions. Each of the test sensor containing regions has a proximal end and a distal end and is adapted to contain a test sensor. The test sensor containing regions protrude radially outward from the center of the housing. The housing has a top portion and a bottom portion that are generally parallel. Each of the test sensors has a width direction and a thickness direction. The first foil cover is adapted to cover the top portion of the housing. The second foil cover is adapted to cover the distal end of the plurality of test sensor containing regions. A plane generally parallel to the width direction of each of the plurality of test sensors is generally perpendicular to the top and bottom portion of the housing.

According to a further embodiment of the present invention, a test sensor packaging container for use in sensor instrument is provided. The test sensor packaging container comprises a molded polymeric housing, a first foil cover, and a second foil cover. The housing has a plurality of test sensor containing regions and a plurality of desiccant cavities in fluid communication with each of the test sensor containing regions. Each of the test sensor containing regions has a proximal end and a distal end and is adapted to contain a test sensor. The test sensor containing regions protrude radially outward from the center of the housing. A plurality of open regions are formed between each of the plurality of test sensor containing regions. The open regions are positioned on the housing to properly position the test sensor packaging container when the test sensor packaging container is in the sensor instrument. The housing has a top portion and a bottom portion that are generally parallel. Each of the test sensors has a width direction and a thickness direction. The first foil cover is adapted to cover the top portion of the housing. The second foil cover is adapted to cover the distal end of the plurality of test sensor containing regions. A plane generally parallel to the width direction of each of the plurality of test sensors is generally perpendicular to the top and bottom portion of the housing.

The above summary of the present invention is not intended to represent each embodiment or every aspect of the present invention. The detailed description and Figures will describe many of the embodiments of the present invention.

DETAILED DESCRIPTION OF THE ILLUSTRATED EMBODIMENT

Figure 1:
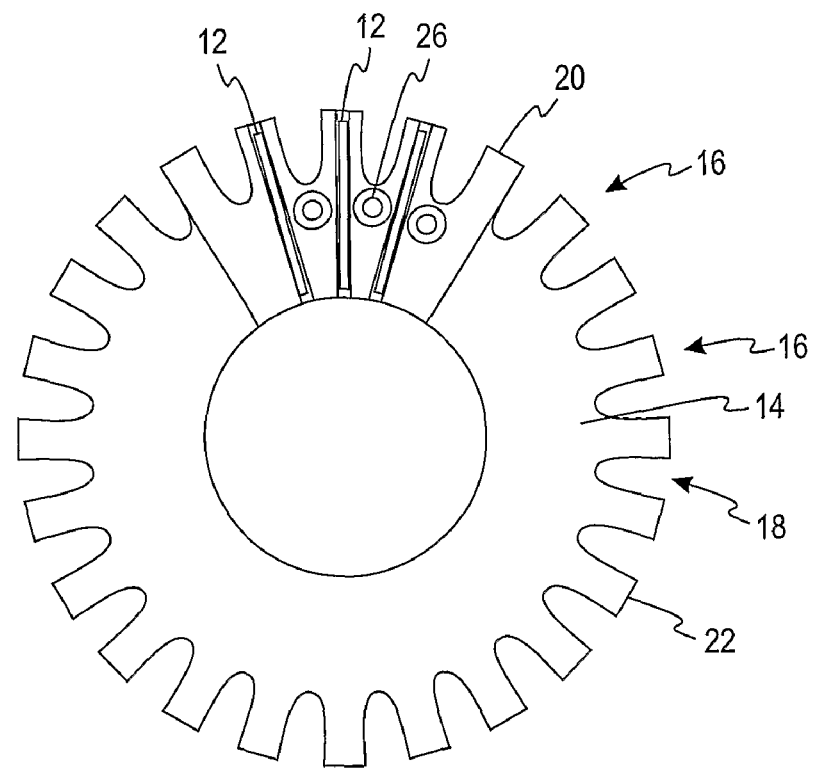
FIG. 1 is a top view of a circular sensor packaging container according to one embodiment of the present invention.

Referring now to the drawings, and initially to FIG. 1, a circular sensor packaging container 10 for holding a plurality of test sensors 12 used in determining a user's analyte concentration level in a fluid sample is shown according to one embodiment of the present invention. While the following discussion describes the use of test sensors for determining the glucose concentration in blood, it is understood that the present invention may be employed in determining the concentration of other analytes in other types of samples. Analytes that may be measured using the present invention include glucose, lipid profiles (e.g., cholesterol, triglycerides, LDL and HDL), microalbumin, hemoglobin $A_{1C}$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine.

The sensor packaging container 10 comprises a housing 14 having a plurality of test sensor containing regions 16. Each of the plurality of test sensor containing regions 16 contains a single test sensor 12. The plurality of test sensor containing regions 16 protrudes out from the center of the housing 14. An open region 18 is formed between each of the plurality of sensor containing regions 16. The sensor containing regions 16 and the open regions 18 forms a generally gear shaped pattern on the sensor packaging container 10. The housing 14 has a first foil cover 20 that is adapted to cover the top portion of the housing 14 of the packaging container 10, sealing the test sensor within the container 10. Additionally, the housing 14 has a second foil cover 22 that is adapted to cover a distal end of the plurality of sensor containing regions 16 of the housing 14, and a third foil cover 24 that is adapted to cover a proximal end of the sensor containing regions 16, further sealing the test sensor within the packaging container 10. The housing 14 and the first, second, and third foil covers 20, 22, 24 completely seal the test sensor 12 from environment.

A plurality of desiccant cavities 26 is in fluid communication with each of the corresponding sensor containing regions 16. Desiccant material is disposed in the desiccant cavities 26 in order to ensure that the sensor containing regions 16 are maintained at an appropriate humidity level so that the reagent material in the test sensor 12 disposed in the particular sensor containing region 16 is not adversely affected prior to being used. The desiccant material might be in the form of a small bag or a bead of material or any other form that can be readily disposed in the plurality of desiccant cavities 26. The desiccant cavities 26 are each in fluid communication with only a single sensor containing region 16. As a result, the opening of one of the sensor containing regions 16 will not affect the desiccated state of any of the other sensor containing regions 16.

Referring still to FIG. 1, the housing 14 of the test sensor packaging container 10 comprises a molded polymeric material according to one embodiment of the present invention. Using a molded polymeric material for the housing 14 increases the structural rigidity of the test sensor packaging container 10. The increased structural rigidity of the housing 14 provided by using a molded polymeric material to form the housing 14 allows the open regions 18 located between each of the plurality of sensor containing regions to be used to align the test sensor packaging container 10 within a testing device, as described in greater detail with respect to FIG. 3.

While FIG. 1 shows the test sensors 12 being oriented such that they are generally normal to a periphery of the test sensor packaging container 10, it is further contemplated that the test sensors may be at an angle of from about five degrees (5°) to about thirty degrees (30°) from normal to the periphery of the test sensor packaging container.

Figure 2:
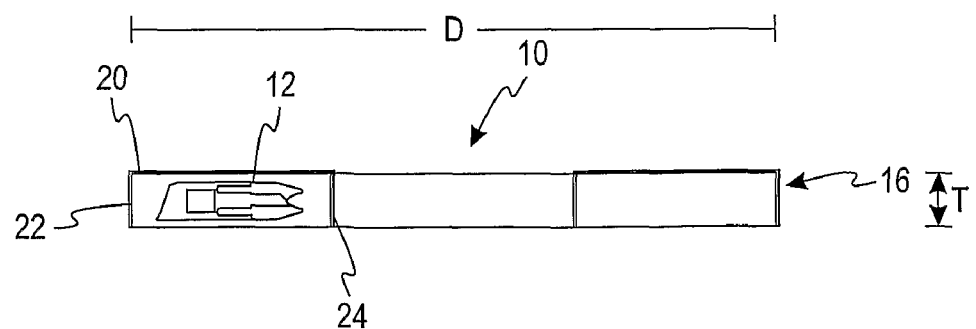
FIG. 2 is a side view of the circular sensor packaging container of FIG. 1.

As is shown in FIG. 2, the test sensor 12 is positioned within the plurality of sensor containing regions 16 of the packaging container 10 such that a plane parallel to the width of the test sensor 12 is perpendicular to the plane of the top portion of the housing 14 of the test sensor packaging container 10. Arranging the test sensor 12 in such a configuration reduces the amount of space along the periphery of the housing 14 required for each test sensor 12 as the test sensors 12 have a width that is greater than their thickness. Therefore, additional test sensors 12 may be placed around a packaging container 10. In this way the diameter of the test sensor packaging container 10 does not dramatically increase in order to increase the number of test sensors 12 held by the test sensor packaging container 10. Increasing the number of test sensors 12 held by the packaging container 10 increases user satisfaction by increasing the number of sample tests that may be performed between changing test sensor packaging containers. The test sensor packaging container 10 is adapted to contain from about twenty five (25) to about thirty five (35) test sensors 12. More specifically, the test sensor packaging container is adapted to contain about thirty (30) test sensors 12. The test sensor packaging container 10 has a diameter D. The diameter D may range from about 40 mm to about 55 mm. More specifically, the diameter D may range from about 45 mm to about 50 mm. The test sensor packaging container 10 has a thickness T. The thickness T of the packaging container 10 may range from about 1 mm to about 3 mm. More specifically, the thickness T of the test sensor packaging container is about 2 mm.

Figure 3A:
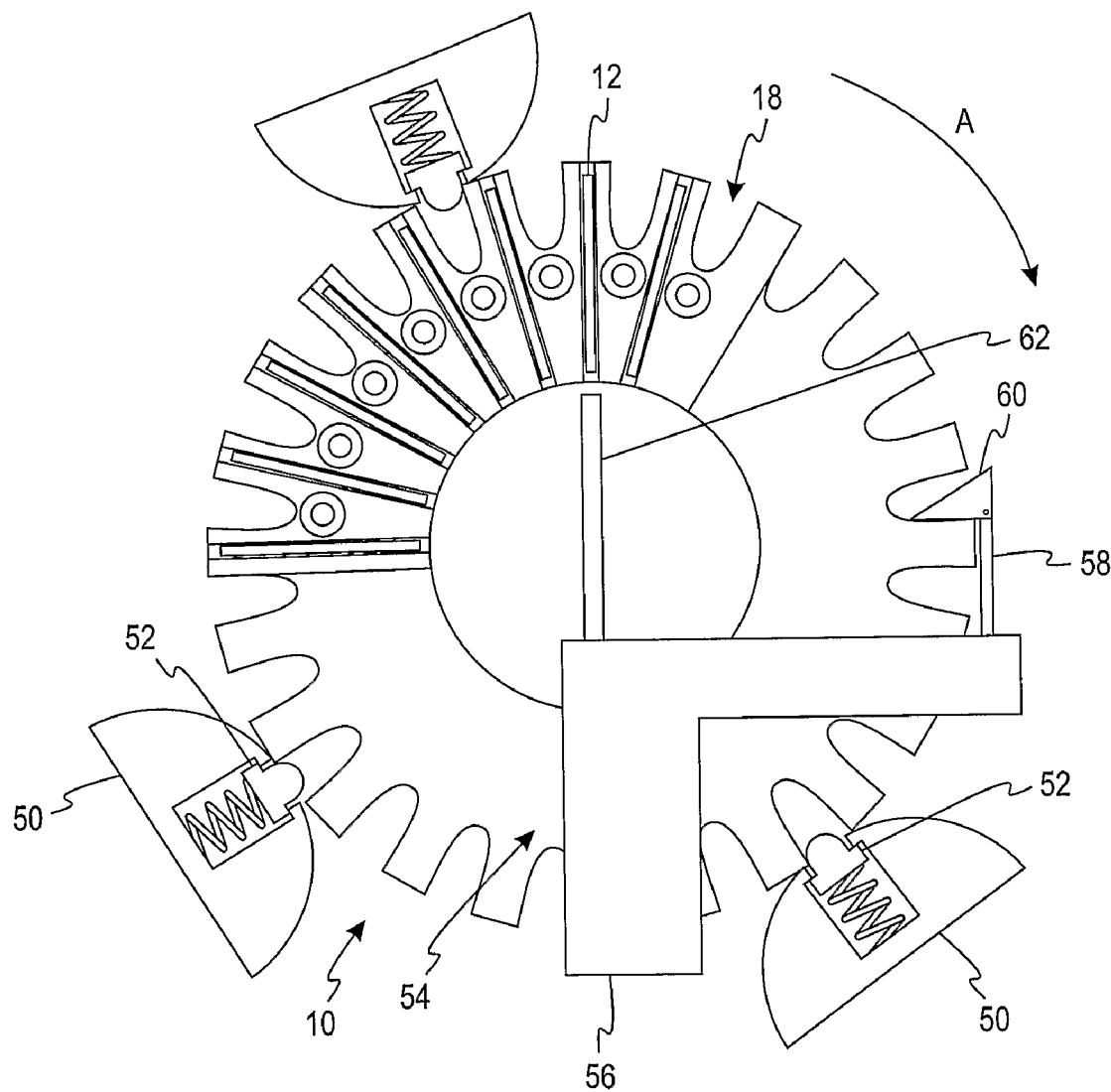
FIG. 3a-c is a top view of the circular sensor packaging container of FIG. 1 within a hand-held test device.

Turning now to FIG. 3a, the test sensor packaging container 10 is shown in conjunction with a plurality of fixture mechanisms 50 of a hand-held testing device. Each of the fixture mechanisms 50 comprises a spring-loaded retaining pin 52. The spring-loaded retaining spring 52 is adapted to fit within the open region 18 of the test sensor packaging container 10 to position the packaging container 10 within the hand-held testing device. The fixture mechanisms 50 allow for precise positioning of the test sensor packaging container within the hand-held testing device. The use of a molded polymeric material for the housing 14 of the packaging container 10 allows the container 10 to be manufactured to a more precise shape than other materials. The packaging container 10 is adapted to rotate within the hand-held testing device to deliver the test sensor from one of the test sensor containing regions 16 of the packaging container 10 to a sample receiving position within the hand-held testing device.

Figure 3B:
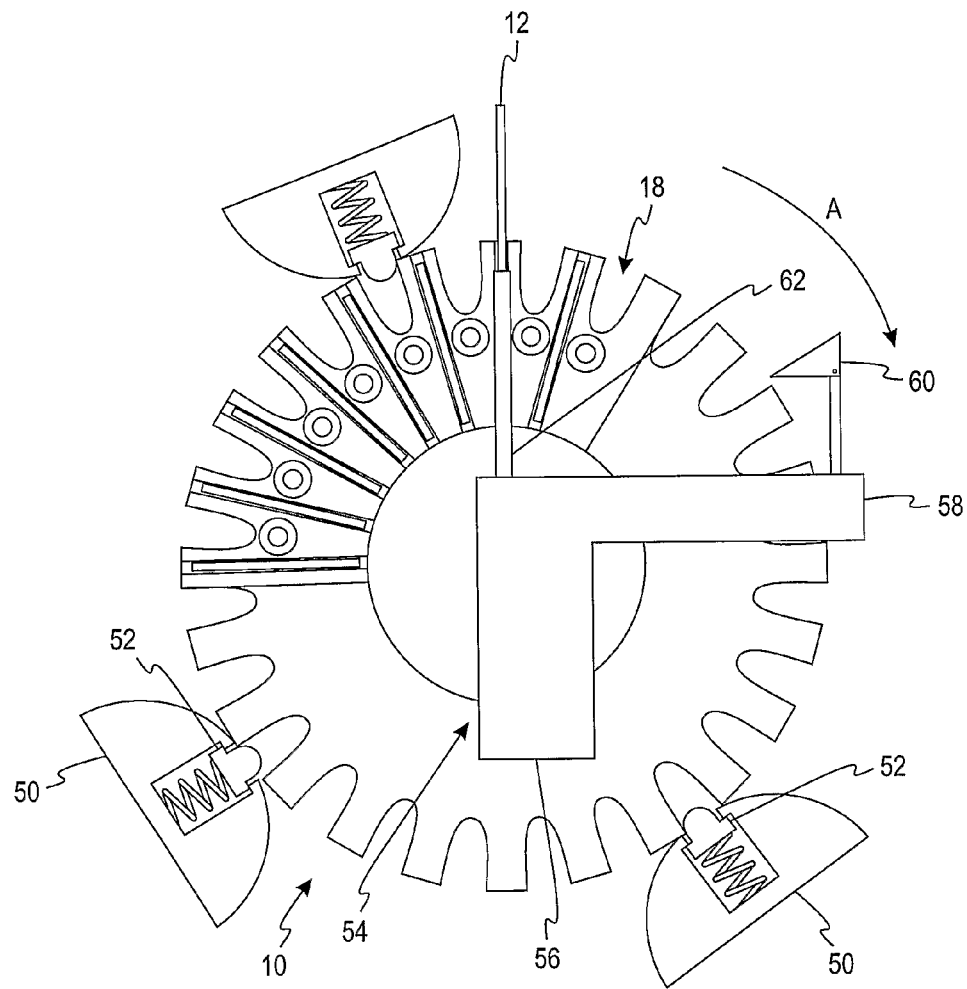
Figure 3C:
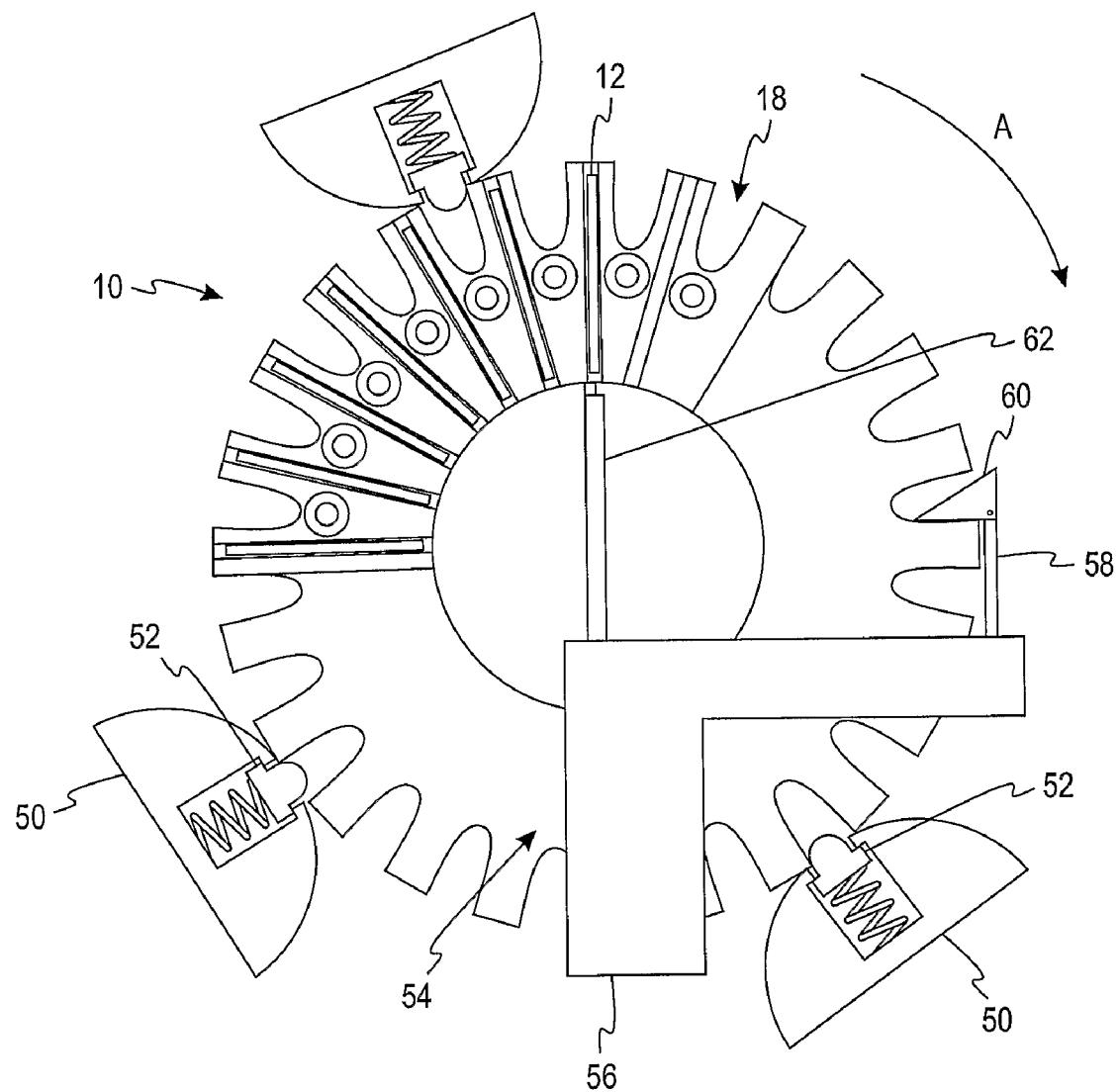

A test sensor dispensing and test sensor packaging container positioning mechanism 54 is also shown in FIGS. 3a-3c. The dispensing and positioning mechanism 54 comprises a slidable dispensing frame portion 56 and a repositioning arm 58. The repositioning arm 58 has a spring loaded engagement element 60 adapted to engage the open region 18 of the test sensor packaging container 10 and rotate the packaging container 10 following the dispensing of a test sensor 12. The spring loaded engagement element 60 is adapted to slide out of the open region 18 it is resting in by having a spring (not shown) be compressed when the dispensing and positioning mechanism 54 is displaced (FIG. 3b). The spring of the engagement element 60 then expands once the engagement element 60 has been removed from the open region it has been resting in, such that it will fit within a next open region 18. As the dispensing and positioning mechanism 54 returns to its original location, the engagement element 60 of the repositioning arm 58 contacts a wall of the open region and rotates the entire sensor packaging container 10 in the direction shown by arrow A so that it is properly positioned to dispense the next test sensor 12 (FIG. 3c).

The slidable dispensing frame portion 56 further comprises a knife portion 62. The knife portion 62 is adapted to contact the test sensor 12 that is to be dispensed from the test sensor packaging container 10. The knife portion 62 punctures the third foil seal 24 and engages the test sensor 12 (FIG. 3b). As the slidable dispensing frame portion 56 continues to be advanced the test sensor 12 slides towards the periphery of the test sensor packaging container 10. The test sensor 12 contacts and punctures the second foil seal 22. The test sensor 12 is thus positioned so that it may be used to analyze a fluid sample.

Figure 4A:
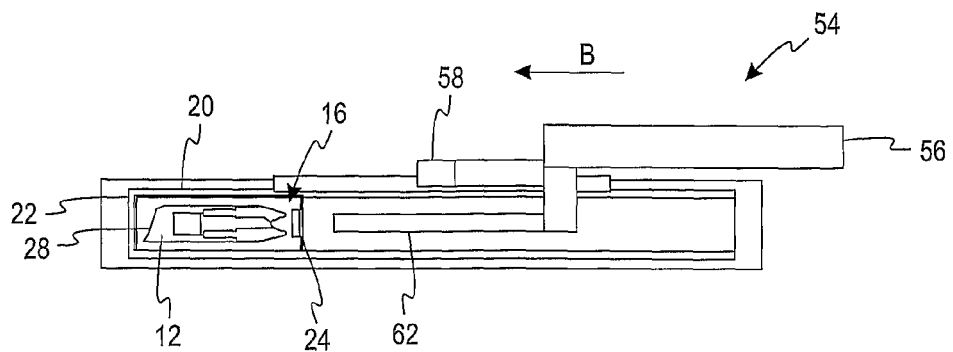
FIGS. 4a-c show a cross-sectional view of a test sensor being dispensed from the circular sensor packaging container of FIG. 1 according to one method of the present invention.
Figure 4B:
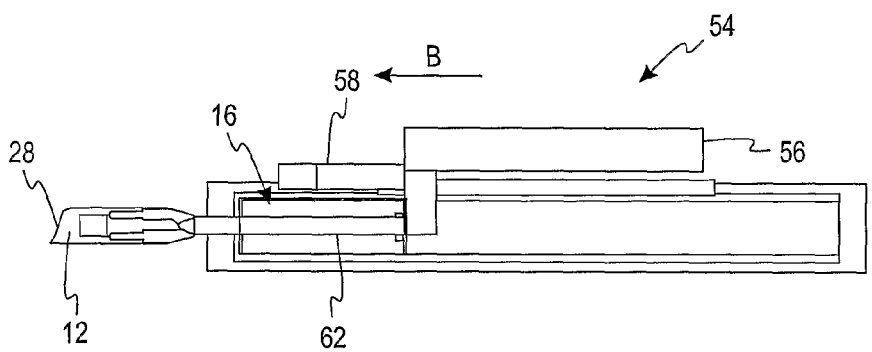
Figure 4C:
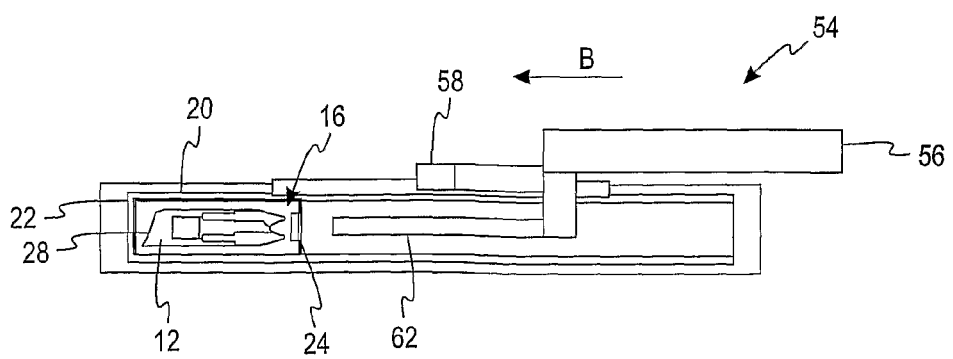

Turning to FIGS. 4a-4c, a side view of the embodiment of FIGS. 3a-3c is shown. As shown in FIG. 4a the knife portion 62 is positioned at a proximal end of one of the plurality of test sensor containing regions 16. The knife portion 62 is adapted to slide outward in a radial direction from the proximal end of one of the plurality of test sensor containing regions 16 towards the distal end of one of the test sensor containing regions. As shown in FIG. 4b, the test sensor 12 is shown after it has been dispensed from the test sensor containing region 16 of the packaging container 10. The knife portion 62 moves in a radial direction along arrow B towards the distal end of the test sensor containing region 16 of the packaging container 10. As the knife portion 62 moves, it initially contacts and punctures the third seal cover 24. As the knife assembly continues to move in the direction of arrow B, it contacts the test sensor 12 forcing the test sensor 12 towards the distal end of the test sensor containing region. The test sensor 12 contains an angled face 28 that contacts the second foil cover 22 of the packaging container 10. The angled face 28 of the test sensor 12 is adapted to puncture the second foil cover 22 of the packaging container 10. FIG. 4c shows the dispensing and positioning mechanism 54 after it has moved in the direction opposite of arrow B back to its original position and rotated the test sensor packaging container 10 so that the next test strip may be dispensed.

Figure 5A:
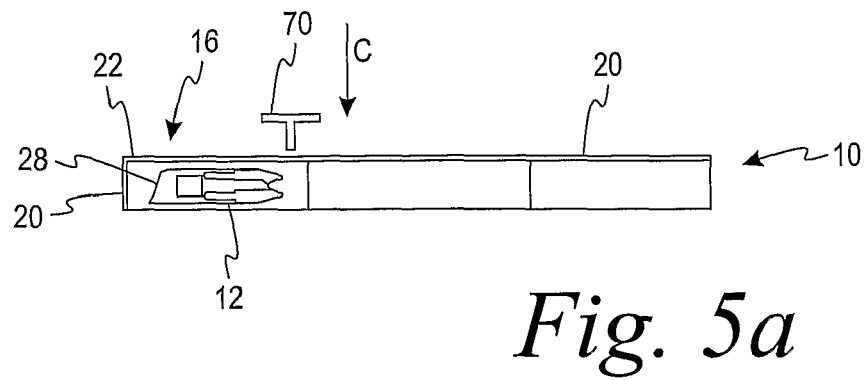
FIGS. 5a-c show a cross-sectional view of a test sensor being dispensed from the circular sensor packaging container of FIG. 1 according to another method of the present invention.
Figure 5B:
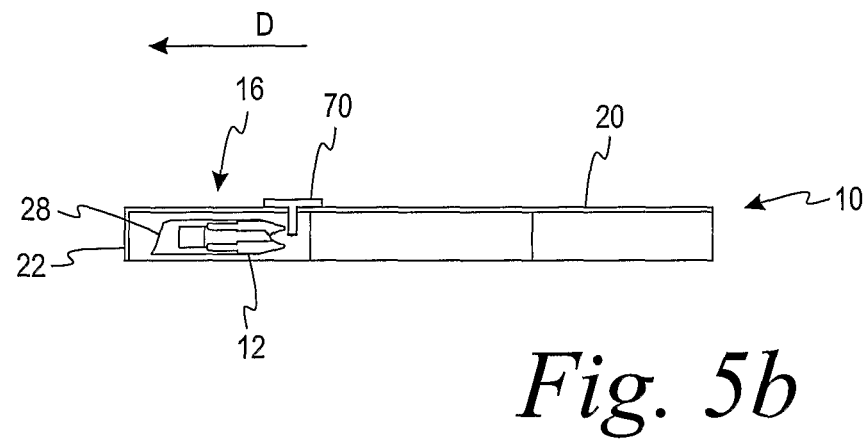
Figure 5C:
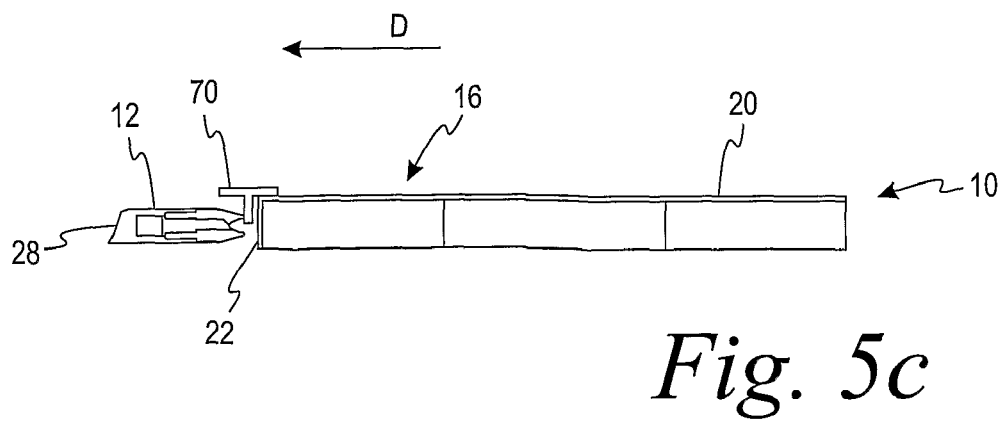

Turning now to FIGS. 5a-c, a side view of the dispensing of one of the test sensors 12 of the test sensor packaging container 10 as described in connection with an alternative embodiment. As seen in FIG. 5a the test sensor packaging container 10 is shown in conjunction with a knife assembly 70. As shown in FIG. 5a the knife assembly 70 has generally a "T" shape, however, other shapes may be used for knife assembly 70. The knife assembly 70 is positioned above the first foil cover 20 of one of the plurality of test sensor containing regions 16. The knife assembly 70 is adapted to move in the direction of arrow C and puncture the first foil cover 20 of the packaging container 10. As shown in FIG. 5b, the knife assembly 70 is positioned to contact and dispense the test sensor 12 after it has punctured the first foil cover 20. FIG. 5c shows the test sensor 12 after it has been dispensed from the test sensor containing region 16 of the packaging container 10. The knife assembly 70 moves in a radial direction along arrow D towards the distal end of the test sensor containing region 16 of the packaging container 10. As the knife assembly 70 moves, it contacts the test sensor 12, forcing the test sensor 12 towards the distal end of the test sensor containing region. The test sensor 12 contains an angled face 28 that contacts the second foil cover 22 of the packaging container 10. The angled face 28 of the test sensor 12 is adapted to puncture the second foil cover 22 of the packaging container 10. As the knife assembly 60 moves in the direction of arrow D it continues to puncture the first foil cover 20 covering the test sensor containing region 16 corresponding to the test sensor 12 being dispensed. Once the test sensor 12 has been dispensed, the knife assembly 70 returns to its initial position as shown in FIG. 5a by moving in the direction opposite of arrow D.

According to another embodiment of the present invention, an information recognition feature is present on a test strip dispensing container. The information recognition feature is positioned on a housing portion of the container. The information recognition feature is adapted to be read by a hand-held testing device to obtain information regarding the test strip dispensing container. It is contemplated that information such as a product code, a production date, an expiration date, a batch number, a test strip model number, and other information may be contained on the information recognition feature. Based on the information contained on the information recognition feature, the hand-held test meter can accept the test sensor packaging container, or reject the test sensor packaging container. As a non-limiting example, it is contemplated that the test meter would reject the packaging container if the expiration date found the information recognition feature has passed. Another example of when the test meter would reject the packaging container is when the test strip model number found on the information recognition feature is not supported by that particular test meter. According to one embodiment, the information recognition feature is a bar code. It is further contemplated that the information recognition feature may be a binary code. It is still further contemplated that the information recognition feature may be a resistance reading system.

Alternative Embodiment A

A test sensor packaging container for use in a sensor instrument for handling a plurality of test sensors, the test sensor packaging container comprising:

a housing having a plurality of test sensor containing regions, each of the plurality of test sensor containing regions having a proximal end and a distal end and being adapted to contain one of the plurality of test sensors, each of the test sensor containing regions protruding radially outward from the center of the housing, the housing having a top portion and a bottom portion that are generally parallel, each of the plurality of test sensors having a width direction and a thickness direction;

a first foil cover adapted to cover the top portion of the housing;

a second foil cover adapted to cover the distal end of the plurality of test sensor containing regions; and a third foil cover adapted to cover the proximal end of the plurality of test sensor containing regions, wherein a plane generally parallel to the width direction of each of the plurality of test sensors is generally perpendicular to the top and bottom portion of the housing.

Alternative Embodiment B

The test sensor packaging container of Alternative Embodiment A further comprising a plurality of open regions formed between each of the plurality of sensor containing regions.

Alternative Embodiment C

The test sensor packaging container of Alternative Embodiment A further comprising a plurality of desiccant cavities in fluid communication with each of the test sensor containing regions.

Alternative Embodiment D

The test sensor packaging container of Alternative Embodiment C further having desiccant material in each of the plurality of desiccant cavities such that each of the test sensor containing regions is maintained in a desiccate state.

Alternative Embodiment E

The test sensor packaging container of Alternative Embodiment B wherein the plurality of test sensor containing regions and the plurality of open regions form a generally gear shaped container, the open regions being positioned on the housing to properly position the test sensor packaging container when the test sensor packaging container is in the sensor instrument.

Alternative Embodiment F

The test sensor packaging container of Alternative Embodiment A wherein the housing has from about twenty five (25) to about thirty five (35) test sensor containing regions.

Alternative Embodiment G

The test sensor packaging container of Alternative Embodiment F wherein the housing has about thirty (30) test sensor containing regions.

Alternative Embodiment H

The test sensor packaging container of Alternative Embodiment A wherein the housing has a diameter from about 40 mm to about 55 mm.

Alternative Embodiment I

The test sensor packaging container of Alternative Embodiment H wherein the housing has a diameter of from about 45 mm to about 50 mm.

Alternative Embodiment J

The test sensor packaging container of Alternative Embodiment A wherein the housing has a thickness of from about 1 mm to about 3 mm.

Alternative Embodiment K

The test sensor packaging container of Alternative Embodiment J wherein the housing has a thickness of about 2 mm.

Alternative Embodiment L

The test sensor packaging container of Alternative Embodiment A wherein the housing of the test sensor packaging container is made of a molded polymeric material.

Alternative Embodiment M

A test sensor packaging container for use in a sensor instrument for handling a plurality of test sensors, the test sensor packaging container comprising:
a housing having a plurality of test sensor containing regions and a plurality of desiccant cavities in fluid communication with each of the test sensor containing regions, each of the plurality of test sensor containing regions having a proximal end and a distal end and being adapted to contain one of the plurality of test sensors, each of the test sensor containing regions protruding radially outward from the center of the housing, the housing having a top portion and a bottom portion that are generally parallel, each of the plurality of test sensors having a width direction and a thickness direction,
wherein a plane generally parallel to the width direction of each of the plurality of test sensors is generally perpendicular to the top and bottom portion of the housing.

Alternative Embodiment N

The test sensor packaging container of Alternative Embodiment M further comprising a plurality of open regions formed between each of the plurality of sensor containing regions.

Alternative Embodiment O

The test sensor packaging container of Alternative Embodiment N wherein the plurality of test sensor containing regions and the plurality of open regions form a generally gear shaped container, the open regions being positioned on the housing to properly position the test sensor packaging container when the test sensor packaging container is in the sensor instrument.

Alternative Embodiment P

The test sensor packaging container of Alternative Embodiment M wherein the housing has from about twenty five (25) to about thirty five (35) test sensor containing regions.

Alternative Embodiment Q

The test sensor packaging container of Alternative Embodiment P wherein the housing has about thirty (30) test sensor containing regions.

Alternative Embodiment R

The test sensor packaging container of Alternative Embodiment M wherein the housing has a diameter from about 40 mm to about 55 mm.

Alternative Embodiment S

The test sensor packaging container of Alternative Embodiment R wherein the housing has a diameter of from about 45 mm to about 50 mm.

Alternative Embodiment T

The test sensor packaging container of Alternative Embodiment M wherein the housing has a thickness of from about 1 mm to about 3 mm.

Alternative Embodiment U

The test sensor packaging container of Alternative Embodiment T wherein the housing has a thickness of about 2 mm.

Alternative Embodiment V

The test sensor packaging container of Alternative Embodiment M wherein the housing of the test sensor packaging container is made of a molded polymeric material.

Alternative Embodiment W

A test sensor packaging container for use in a sensor instrument for handling a plurality of test sensors, the test sensor packaging container comprising:
a molded polymeric housing having a plurality of test sensor containing regions and a plurality of desiccant cavities in fluid communication with each of the test sensor containing regions, each of the plurality of test sensor containing regions having a proximal end and a distal end and being adapted to contain one of the plurality of test sensors, a plurality of open regions formed between each of the plurality of sensor containing regions, the open regions being positioned on the housing in order to properly position the test sensor packaging container when the test sensor packaging container is in the sensor instrument, the housing having a top portion and a bottom portion that are generally parallel, each of the plurality of test sensors having a width direction and a thickness direction;
a first foil cover adapted to cover the top portion of the housing; and
a second foil cover adapted to cover the distal end of the plurality of test sensor containing regions,
wherein a plane generally parallel to the width direction of each of the plurality of test sensors is generally perpendicular to the top and bottom portion of the housing.

Alternative Embodiment X

The test sensor packaging container of Alternative Embodiment W wherein the housing has from about twenty five (25) to about thirty five (35) test sensor containing regions.

Alternative Embodiment Y

The test sensor packaging container of Alternative Embodiment X wherein the housing has about thirty (30) test sensor containing regions.

Alternative Embodiment Z

The test sensor packaging container of Alternative Embodiment W wherein the housing has a diameter from about 40 mm to about 55 mm.

Alternative Embodiment AA

The test sensor packaging container of Alternative Embodiment Z wherein the housing has a diameter of from about 45 mm to about 50 mm.

Alternative Embodiment BB

The test sensor packaging container of Alternative Embodiment W wherein the housing has a thickness of from about 1 mm to about 3 mm.

Alternative Embodiment CC

The test sensor packaging container of Alternative Embodiment BB wherein the housing has a thickness of about 2 mm.

Alternative Embodiment DD

The test sensor packaging container of Alternative Embodiment W wherein the plurality of test sensor containing regions is generally normal to a periphery of the polymeric housing.

Alternative Embodiment EE

The test sensor packaging container of Alternative Embodiment W wherein the plurality of test sensor containing regions is arranged at an angle of about less than thirty degrees from normal to a periphery of the polymeric housing.

Alternative Embodiment FF

The test sensor packaging container of Alternative Embodiment W wherein the plurality of test sensor containing regions is arranged at an angle of about more than five degrees to about less than thirty degrees from normal to a periphery of the polymeric housing.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined in the appended claims.

The invention claimed is:
1. A test sensor packaging container for use in a sensor instrument, the test sensor packaging container comprising:
a plurality of test sensors, each of the plurality of test sensors having a length, a width, and a thickness, the thickness of the test sensors being smaller than the width, the length and the width defining a top surface and a bottom surface;
a housing having a top portion and a bottom portion that are generally parallel and a plurality of test sensor containing regions positioned therebetween, each of the plurality of test sensor containing regions having a proximal end and a distal end and containing one of the plurality of test sensors therein such that a plane generally parallel to the top surface and the bottom surface of any one of the plurality of test sensors is generally perpendicular to the top and the bottom portions of the housing, each of the test sensor containing regions protruding radially outward from the center of the housing, a plurality of open regions formed between each of the plurality of test sensor containing regions, the open regions being positioned on the housing to properly position the test sensor packaging container in response to the test sensor packaging container being in the sensor instrument;

a first foil cover adapted to cover the top portion of the housing;

a second foil cover adapted to cover the distal end of the plurality of test sensor containing regions and adapted to be bursted only by an edge of the plurality of test sensors; and a third foil cover adapted to cover the proximal end of the plurality of test sensor containing regions, wherein the distal end and the proximal end of the plurality of test sensor containing regions are positioned between the top and the bottom portions of the housing.

2. The test sensor packaging container of claim 1, further comprising a plurality of desiccant cavities in fluid communication with each of the test sensor containing regions.

3. The test sensor packaging container of claim 2, further having desiccant material in each of the plurality of desiccant cavities such that each of the test sensor containing regions is maintained in a desiccate state.

4. The test sensor packaging container of claim 1, wherein the plurality of test sensor containing regions and the plurality of open regions form a generally gear shaped container.

5. The test sensor packaging container of claim 1, wherein the housing has from about twenty five (25) to about thirty five (35) test sensor containing regions.

6. The test sensor packaging container of claim 1, wherein the housing has a diameter from about 40 mm to about 55 mm.

7. The test sensor packaging container of claim 1, wherein the housing has a thickness of from about 1 mm to about 3 mm.

8. The test sensor packaging container of claim 1, wherein the housing of the test sensor packaging container is made of a molded polymeric material.

9. A test sensor packaging container for use in a sensor instrument, the test sensor packaging container comprising:

a plurality of test sensors, each of the plurality of test sensors having a length, a width, and a thickness, the thickness of the test sensors being smaller than the width, the length and the width defining a top surface and a bottom surface;

a housing having a top portion and a bottom portion that are generally parallel and a plurality of test sensor containing regions positioned therebetween, each of the plurality of test sensor containing regions having a proximal end and a distal end and containing one of the plurality of test sensors therein such that a plane generally parallel to the top surface or the bottom surface of any one of the plurality of test sensors is generally perpendicular to the top and the bottom portions of the housing; and a foil cover adapted to cover the distal end of the plurality of test sensor containing regions and adapted to be bursted by an edge of at least one of the plurality of test sensors, wherein the distal end and the proximal end of the plurality of test sensor containing regions are positioned between the top and the bottom portions of the housing.

10. The test sensor packaging container of claim 9, wherein the plurality of test sensor containing regions and the plurality of open regions form a generally gear shaped container, the open regions being positioned on the housing to properly position the test sensor packaging container when the test sensor packaging container is in the sensor instrument.

11. The test sensor packaging container of claim 9, wherein the housing has from about twenty five (25) to about thirty five (35) test sensor containing regions.

12. The test sensor packaging container of claim 9, wherein the housing has a diameter from about 40 mm to about 55 mm.

13. The test sensor packaging container of claim 9, wherein the housing has a thickness of from about 1 mm to about 3 mm.

14. The test sensor packaging container of claim 9, wherein the housing of the test sensor packaging container is made of a molded polymeric material.

15. The test sensor packaging container of claim 9, wherein each of the plurality of test sensor containing regions has a length between the proximal end and the distal end, a width, and a depth, the width of each of the test sensor containing regions being generally constant along the length.

16. A test sensor packaging container for use in a sensor instrument, the test sensor packaging container comprising:

a plurality of test sensors, each of the plurality of test sensors having a length, a width, and a thickness, the thickness of the test sensors being smaller than the width, the length and the width defining a top surface and a bottom surface;

a molded polymeric housing having a top portion and a bottom portion that are generally parallel, the housing having a plurality of test sensor containing regions and a plurality of desiccant cavities in fluid communication with each of the test sensor containing regions positioned between the top and the bottom portions of the housing, each of the plurality of test sensor containing regions has a proximal end and a distal end and contains one of the plurality of test sensors therein such that a plane generally parallel to the top surface and the bottom surface of any one of the plurality of test sensors is generally perpendicular to the top and the bottom portions of the housing, a plurality of open regions formed between each of the plurality of test sensor containing regions, the open regions being positioned on the housing in order to properly position the test sensor packaging container when the test sensor packaging container is in the sensor instrument;

a first foil cover adapted to cover the top portion of the housing; and a second foil cover adapted to cover the distal end of the plurality of test sensor containing regions and adapted to be bursted by an edge of at least one of the plurality of test sensors, wherein the distal end of the plurality of test sensor containing regions is positioned between the top and the bottom portion of the housing.

17. The test sensor packaging container of claim 16, wherein the housing has from about twenty five (25) to about thirty five (35) test sensor containing regions.

18. The test sensor packaging container of claim 16, wherein the housing has a diameter from about 40 mm to about 55 mm.

19. The test sensor packaging container of claim 16, wherein the housing has a thickness of from about 1 mm to about 3 mm.

20. The test sensor packaging container of claim 16, wherein the plurality of test sensor containing regions is generally normal to a periphery of the polymeric housing.

21. The test sensor packaging container of claim 16, wherein the plurality of test sensor containing regions is arranged at an angle of about less than thirty degrees from normal to a periphery of the polymeric housing.

22. The test sensor packaging container of claim 16, wherein the plurality of test sensor containing regions is arranged at an angle of about more than five degrees to about less than thirty degrees from normal to a periphery of the polymeric housing.

* * * * *